US008969470B1

(12) United States Patent
Li (10) Patent No.: US 8,969,470 B1
(45) Date of Patent: Mar. 3, 2015

(54) QUANTUM DOT-POLYMER NANOCOMPOSITE FOR OPTICAL SENSING

(71) Applicant: Sichu Li, Fairfax, VA (US)

(72) Inventor: Sichu Li, Fairfax, VA (US)

(73) Assignee: The Mitre Corporation, McLean, VA (US)

( * ) Notice: Subject to any disclaimer, the term of this patent is extended or adjusted under 35 U.S.C. 154(b) by 0 days.

(21) Appl. No.: 13/915,701

(22) Filed: Jun. 12, 2013

(51) Int. Cl.
*G01N 21/64* (2006.01)
*C08L 25/00* (2006.01)
*C08L 33/00* (2006.01)
*B82Y 99/00* (2011.01)
*H01L 21/00* (2006.01)

(52) U.S. Cl.
CPC .............. *G01N 21/6428* (2013.01); *B82Y 99/00* (2013.01); *Y10S 438/982* (2013.01)
USPC ............. 524/556; 438/82; 438/982; 257/441; 257/465; 257/466

(58) Field of Classification Search
CPC ......... C08L 25/00; C08L 33/00; C08L 67/02; C08L 29/00; C08L 23/00; H01L 21/00; H01L 31/00; G01N 21/6428
USPC ............. 524/556; 438/82, 962; 257/441, 465, 257/466
See application file for complete search history.

(56) References Cited

FOREIGN PATENT DOCUMENTS

CN      101759946 A  *  6/2010

OTHER PUBLICATIONS

Vassiltsova et al. "Synthesis of Nanocomposite Materials with Controlled Structures and Optical Emissions: Application of Various Methacrylate Polymers for CdSe Quantum Dots Encapsulation", Journal of Nanoscience and Nanotechnology, vol. 10, 1635-1642, 2010.*
Gorelikov I, Kumacheva E. Electrodeposition of polymersemiconductor nanocomposite films. Chem Mater 2004; 16:4122-7.
Kaushik D, Sharma M, Singh RR, Gupta DK, Pandey RK. Synthesis and characterisation of electropolymerised polyaniline/Q-ZnSe composite films. Mater Lett 2006; 60:2994-7.
Gao My, Yang Y, Yang B, Bian FL, Shen JC. Synthesis of PbS nanoparticles in polymer matrices. Chem Commun 1994: 2779-80.
Yang Y, Huang JM, Liu SY, Shen JC. Preparation, characterization and electroluminescence of ZnS nanocrystals in a polymer matrix. J Mater Chem 1997; 7:131-3.
Yang Y, Huang JM, Yang B, Liu SY, Shen JC. Electroluminescence from ZnS/CdS nanocrystals/polymer composite. Synth Met 1997; 91:347-9.
Lü CL, Guan C, Liu YF, Cheng YR, Yang B. PbS/polymer nanocomposite optical materials with high refractive index. Chem Mater 2005; 17:2448-54.
Wang JY, ChenW, Liu AH, Lu G, Zhang G, Zhang JH, et al. Controlled fabrication of cross-linked nanoparticles/polymer composite thin films through the combined use of surface-initiated atom transfer radical polymerization and gas/solid reaction. J Am Chem Soc 2002; 124:13358-9.
Cui T, Zhang JH, Wang JY, Cui F, Chen W, Xu FB, et al. CdS-nanoparticle/polymer composite shells grown on silica nanospheres by atom transfer radical polymerization. Adv Funct Mater 2005; 15:481-6.
Salata OV, Dobson PJ, Hull PJ, Hutchinson JL. Fabrication of PbS nanoparticles embedded in a polymer film by a gas-aerosol reactive electrostatic deposition technique. Adv Mater 1994; 6:772-5.
Salata OV, Dobson PJ, Hull PJ, Hutchison JL. Uniform GaAs quantum dots in a polymer matrix. Appl Phys Lett 1994; 65:189-91.
Salata OV, Dobson PJ, Hull PJ, Hutchison JL. Fabrication of CdS nanoparticles embedded in a polymer film by gas aerosol reactive electrostatic deposition technique. Thin Solid Films 1994; 251:1-3.
Wang Y, Suna A, Mahler W, Kasowski R. PbS in polymers. From molecules to bulk solids. J Chem Phys 1987; 87:7315-22.
Lee J, Sundar VC, Heine JR, Bawendi MG, Jensen KF. Full color emission from II-VI semiconductor quantum dot—polymer composites. Adv Mater 2000; 12:1102-5.
Pang L, Shen Y, Tetz K, Fainman Y. PMMA quantum dots composites fabricated via use of pre-polymerization. Opt Express 2005; 13:44-9.
Martiradonna L, Stomeo T, De Giorgi M, Cingolani R, DeVittorio M. Nanopatterning of colloidal nanocrystals emitters dispersed in a PMMA matrix by e-beam lithography. Microelectr Eng 2006; 83:1478-81.
Ballou B, Lagerholm BC, Ernst LA, Bruchez MP, Waggoner AS. Noninvasive imaging of quantum dots in mice. Bioconjugate Chem 2004; 15:79-86.
Gao X, Cui Y, Levenson RM, L. Chung WK and Nie S. In-vivo cancer targeting and imaging with semiconductor quantum dots, Nature Biotechnology 2004; 22:969-976.

(Continued)

*Primary Examiner* — Michael M Bernshteyn
(74) *Attorney, Agent, or Firm* — Rosenburg, Klein & Lee (57) ABSTRACT

A quantum dot-polymer nanocomposite for optical chemical and biological sensing is formed by stably incorporating functionalized quantum dots into a pH sensitive hydrogel polymer network. At least one monomer of the pH sensitive hydrogel has functional groups selectively chosen to correspond to functionalized groups on the quantum dots to enable conjugation between the hydrogel polymer network and the functionalized quantum dots. The resulting quantum dot-polymer nanocomposite is placed in a solution having a known pH and addition of a chemical composition or biological agent of interest generates a change in pH of that solution. The nanocomposite expands or contracts responsive to the pH change. The pH change is optically detected by measuring the intensity level of fluorescence from the quantum dots when the nanocomposite is subjected to an excitation light source.

17 Claims, 5 Drawing Sheets

(56) References Cited

OTHER PUBLICATIONS

Han My, Gao X, Su JZ and Nie S. Quantum-Dot-Tagged Microbeads for Multiplexed Optical Coding of Biomolecules, Nature Biotechnology 2001; 19:631-635.

Guo GN, Liu W, Liang JG, Xu HB, He ZK, Yang XL. Preparation and characterization of novel CdSe quantum dots modified with poly (d,l-lactide) nanoparticles. Mater Lett 2006; 60:2565-8.

Michalet X, Pinaud FF, Bentolila LA, Tsay JM, Doose S, Li JJ, et al. Quantum dots for live cells, in vivo imaging, and diagnostics. Science 2005; 307:538-44.

Sharma P, Brown S, Walter G, Santra S, Moudgil B. Nanoparticles for bioimaging. Adv Colloid Interface Sci 2006; 123:471-85.

Mulvaney SP, Mattoussi H, Whitman LJ. Incorporating fluorescent dyes and quantum dots into magnetic microbeads for immunoassays. BioTechniques 2004; 36:602-9.

Rosenthal SJ. Bar-coding biomolecules with fluorescent nanocrystals. Nat Biotechnol 2001; 19:621-2.

Gaponik N, Radtchenko IL, Sukhorukov GB, Weller H, Rogach AL. Toward encoding combinatorial libraries: charge-driven microencapsulation of semiconductor nanocrystals luminescing in the visible and near IR. Adv Mater 2002; 14:879-82.

Kirchner C, Munóz Javier A, Susha AS, Rogach AL, Kreft O, Sukhorukov GB, et al. Cytotoxicity of nanoparticle-loaded polymer capsules. Talanta 2005; 67:486-91.

Zebli B, Susha AS, Sukhorukov GB, Rogach AL, Parak WJ. Magnetic targeting and cellular uptake of polymer microcapsules simultaneously functionalized with magnetic and luminescent nanocrystals. Langmuir 2005; 21:4262-5.

R. Bashir, et al., Micromechanical Cantilever as an Ultrasensitive pH Microsensor, Appl. Phys. Lett. 81 (2002) 3091-3093.

C. Ruan, et al., A Mass-Sensitive pH Sensor Based on a Stimuli Responsive Polymer, Anal. Chem. Acta. 497 (2003) 123-131.

M. Kuang, et al., Fabrication of Multicolor-Encoded Microspheres by Tagging Semiconductor Nanocrystals to Hydrogel Spheres, Advanced Materials 17 (2005) 267-270.

\* cited by examiner

QUANTUM DOT-POLYMER NANOCOMPOSITE FOR OPTICAL SENSING

FIELD OF THE INVENTION

The subject invention relates generally to the field of optical sensing. In particular, the invention relates to a novel nanocomposite for optical chemical and biological sensing applications. More specifically, the invention relates to incorporating quantum dots into a polymer network, specifically a hydrogel polymer network, whereby changes in fluorescence can be measured or exploited for detecting the presence or a change in concentration of particular chemical compositions and biological agents of interest. Several alternative nanocomposites and methods for their synthesis, as well as the method of using these nanocomposites to detect changes in the pH of a solution, resulting from the introduction of the chemical composition or biological agent, by measuring changes in detected quantum dot fluorescence from the nanocomposite are presented.

BACKGROUND OF THE INVENTION

Field of the Invention

The present disclosure relates generally to quantum dot-polymer nanocomposites for optical chemical and biological sensing. In particular, the subject application relates to hydrogel polymer nanocomposites wherein quantum dots are stably incorporated therein. More in particular, the subject application relates to the conjugation of quantum dots to a hydrogel polymer network. Thereby, the quantum dots serve as an optical indicator of physical changes in the hydrogel polymer network as a reaction to changes in pH of a solution. By this configuration, changes in fluorescence can be measured or exploited for detecting the presence or a change in concentration of particular chemical compositions or biological agents of interests whose presence changes the pH of the solution. As pH of the solution being monitored changes, the hydrogel polymer nanocomposite changes in physical size (expands or contracts) and in correspondence thereto the measured quantum dot fluorescence changes.

Quantum Dots (QDs) are semiconductor nanocrystals which are known for their unique size-tunable optical and electronic properties. For the past few decades, extensive amounts of time, energy, and funding have been devoted to research and development efforts exploring the use of quantum dots (QDs) in a variety of different areas, for example, biological labeling for imaging and monitoring and optical sensing for chemical and biological detection. In the context of chemical and biological sensing applications, QDs must be functionalized on their surfaces, or embedded in a solid state matrix to form a composite. This is necessary to avoid QD agglomeration and the consequent fluorescence quenching.

Attributed to their transparence in the ultraviolet-visible (UV-Vis) region of the electromagnetic spectrum, polymeric materials are suitable candidates to be utilized as matrices for quantum dot composites in optical sensing applications.

A specific class of polymers, namely, hydrogel polymers has the ability to expand or shrink when subjected to external stimuli responsive to the repulsion or attraction of the polymer network in a particular solvent. Hydrogel polymers may include a variety of different functional groups on their backbone chains. Depending on whether the functional groups are acidic or basic, such will dictate the polymer network's response to different pH conditions of a solution. Such changes have been detected by a variety of sensing methods based on different transduction principles. For instance, changes in surface stress due to the expansion of the polymer network have been measured using atomic force microscopy. (R. Bashir, et al., *Micromechanical Cantilever as an Ultrasensitive pH Microsensor*, Appl. Phys. Lett. 81 (2002) 3091-3093). Additionally, changes in mass have been measured with a quartz crystal microbalance. (C. Ruan, et al., *A Mass-Sensitive pH Sensor Based on a Stimuli Responsive Polymer*, Anal. Chem. Acta. 497 (2003) 123-131; X. Li, *A Quartz Crystal Sensor for monitoring Polymerization, Expansion and Contraction of a Contractible Body*, 8th Pacific Centre for Advanced Materials and Microstructures, Burnaby, BC, Canada. Dec. 6, 2003).

Notwithstanding the aforementioned research efforts related to measurable changes of hydrogels themselves, research and development in QD-polymer composites for chemical and biological sensing has remained largely unexplored.

By incorporating quantum dots into a hydrogel polymer network structure to form a nanocomposite, the quantum dots act as optical indicators for optical sensing applications. In solution, as the polymer network is subjected to changes in pH, the network will shrink or expand, resulting in a change in detected fluorescence of the quantum dots in the nanocomposite.

Previous studies have demonstrated that QDs can be trapped inside a specific type of hydrogel polymer network, namely, PNIPAM-co-PVP, under certain pH conditions. (M. Kuang, et al., *Fabrication of Multicolor-Encoded Microspheres by Tagging Semiconductor Nanocrystals to Hydrogel Spheres*, Advanced Materials 17 (2005) 267-270). However, it was determined that as the polymer network structure was caused to contract under certain pH conditions, quantum dots were released from the polymer network structure. Such results indicate that the quantum dots were not stably incorporated into the PNIPAM-co-PVP network.

SUMMARY OF THE INVENTION

A quantum dot-polymer nanocomposite is provided that includes a plurality of quantum dots stably incorporated into a hydrogel network known to be physically responsive to pH changes. The network is formed from a mixture of acrylic family monomers using a cross-linking agent. When the nanocomposite is in contact with a solution having a known pH, the addition of a biological or chemical target of interest generates a change in pH of the solution and thereby causes an expansion or contraction of the hydrogel polymer network. A light scattering effect of the polymer network and spacing between the plurality of quantum dots each change in correspondence to the expansion or contraction of the hydrogel polymer network and results in a change in fluorescence emission intensity. Thereby, the change in pH is detected by measuring the change in quantum dot fluorescence emission intensity.

In another aspect, a nanocomposite is formed of a plurality of quantum dots distributed within a hydrogel polymer network known to be physically responsive to pH changes. The quantum dots are functionalized to chemically bond to the hydrogel polymer network. The nanocomposite is in contact with a solution having a known pH and addition of a biological or chemical target of interest generates a change in pH of the solution thereby causing an expansion or contraction of the hydrogel polymer network. A light scattering effect of the polymer network and spacing between the plurality of quantum dots each change in correspondence to the expansion or contraction of the hydrogel polymer network and results in a change in fluorescence emission intensity. Thereby, changes in pH are detected by measuring the change in quantum dot fluorescence.

From another aspect, a method of forming the QD-polymer nanocomposite begins with the step of obtaining a quantum dot suspension and at least an acrylic monomer, an acrylate monomer and a cross linking agent. The quantum dot suspension is dried until the suspension becomes wax-like and then, the quantum dots are dried in the acrylic monomer as a component of a precursor solution for polymerization to form a polymer network. The method further includes preparing the precursor solution containing the acrylic monomer with dissolved quantum dots, the acrylate monomer, the cross-linking agent and a photoinitiator. Then, a predetermined volume of the precursor solution is placed on a surface or in a container and cured to form the quantum-dot polymer nanocomposite.

From yet another aspect, a method of forming a QD-polymer nanocomposite begins with the step of obtaining a quantum dot suspension, an acrylic monomer and an acrylate monomer. The quantum dot suspension is dried until the suspension becomes wax-like and then, the quantum dots are dissolved in a solvent which may be selected from the group consisting of, acetone and dimethyl sulfoxide (DMSO). The dried quantum dot suspension is mixed with the monomers, a cross-linking agent and a photoinitiator to form the precursor solution for polymerization. At least a portion of the precursor solution is placed on a surface or in a container. Then, the precursor solution is cured to form the quantum dot-polymer nanocomposite.

From a further aspect, a method of stably incorporating quantum dots into a copolymer network is provided wherein first, the quantum dots having surface functionalized groups selected from the group consisting of amine, carboxyl and hydroxyl are obtained. The quantum dots are dried and then the quantum dots are dissolved in a monomer. Next, a precursor solution is prepared. The precursor solution comprises one acrylic monomer and one acrylate monomer. At least one of the acrylic monomer and the acrylate monomer has functional groups selected from the group consisting of amine, carboxyl and hydroxyl selected to bond with the functionalized quantum dots. Then, polymerization is conducted to generate a copolymer network. Thereby, chemical interaction of the functional groups on the surface of the quantum dots and the at least one of the acrylic monomer and the acrylate monomer enables conjugation between the quantum dots and the copolymer network.

From still another aspect, a system for detecting the biological and chemical presence or change in a solution is provided. The system comprises a solution in which the biological or chemical presence or change in concentration is to be detected and a quantum dot-polymer nanocomposite exposed to this solution. A plurality of quantum dots are stably incorporated into a polymer network and the polymer network expands or contracts in response to a change in pH of the solution resulting from the change in concentration or presence of the biological agent or chemical composition. The system further includes an excitation light source with a wavelength range that overlaps with the excitation wavelength range of the quantum dots in the nanocomposite, e.g. wavelengths in the range of 300 to 450 nm. Additionally, the system includes an optical detection system positioned to collect fluorescence from quantum dots in the nanocomposite and measure changes in the fluorescence as the polymer network expands or contracts.

From yet another aspect, the present invention is directed to a quantum dot-polymer nanocomposite for optical sensing which comprises a plurality of quantum dots stably incorporated into a pH-sensitive hydrogel polymer network. The quantum dot-polymer nanocomposite is in contact with a solution having a known pH, wherein addition of a biological or chemical target of interest generates a change in pH of the solution and a corresponding expansion or contraction of the hydrogel polymer network. Light scattering effect of the polymer network and spacing between the plurality of quantum dots changes in correspondence to the expansion or contraction of the hydrogel polymer network. This results in a change in a fluorescence emission intensity in response to impingement by an excitation light source. The change in pH is thereby detected by measuring the change in quantum dot fluorescence emission intensity.

DETAILED DESCRIPTION OF THE PREFERRED EMBODIMENTS

In general, the terms and phrases used herein have their art-recognized meaning, which can be found by reference to standard texts, journal references, and context known to those skilled in the art. The following definition is provided to clarify its specific use in context of the disclosure.

"Conjugation" as used herein refers to the joining together of two compounds to create a new compound. More specifically, it refers to two reactive functional groups which, by covalent attachment, form a new chemical structure.

As used herein, the terms "shrink," "shrinkage," "contract" and "contraction" are synonymous and intended to mean a reduction in physical size.

The following details are intended to explain the inventive concept of the subject Patent Application. However, such are provided for illustrative purposes and not intended to limit the scope of the invention. It will be apparent to those skilled in the art that a number of substitutions of, for example, chemical compounds may be made without departing from the scope of the invention.

In general concept, the QD-polymer nanocomposite for optical sensing comprises a plurality of quantum dots which are stably incorporated into a hydrogel polymer network known to physically expand or contract responsive to pH changes. At least one monomer, of which the pH sensitive hydrogel is comprised of, has functionalized groups which are selectively chosen to correspond to functionalized groups on the quantum dots to be stably incorporated in nanocomposite. Thereby, the quantum dots will be conjugated to the polymer network structure due to chemical bonding formed via a chemical reaction between the functionalized groups of at least one of the monomers of the polymer network and the quantum dots.

When the quantum dot polymer nanocomposite is placed in solution having a known pH, addition of a chemical or biological target of interest generates a change in pH of that solution, thereby resulting in the expansion or contraction of the polymer network structure. The solution is an aqueous solution which may initially have a pH within the range of 4-7. When the polymer network has acidic functional groups, for example, addition of a chemical or biological target which creates a more acidic environment leads to a change in the physical size (expansion or contraction) of the polymer network structure. Alternatively, when the pH is increased by addition of a particular target, the more alkaline environment results in an opposite change in the physical size of the polymer network structure.

When subjected to an excitation light source, a contracting polymer network results in an increase in internal scattering of excitation and emission light. Thus, there will be a lower intensity in the observed fluorescence attributed to the emission of the quantum dots. On the other hand, expansion of the polymer network results in an increase in fluorescence intensity.

The nanocomposites can be applied to a wide array of biological and chemical sensing applications. In terms of chemical sensing, the QD-polymer nanocomposites can be utilized to monitor chemical reactions that yield a pH change. For chemical reactions that involve a change in pH of the reaction media, the nanocomposites can continuously measure the pH. Thereby, the progress of a reaction can be actively monitored.

An exemplary biological detection application is monitoring growth of microorganisms. A large number of microorganisms produce citric acid in a fermentation medium. Such microorganisms include *Yarrowia lipolytica, Aspergillus niger, Candida (Yarrowia) lipolytica, Candida guilliermondii, Candida oleophila, Candida intermedia, Candida paratropicalis, Candida zeylanoides, Candida catenulata, Candida parapsilosis, Pichia anomala*, and some *Rhodotorula* species. By continuously monitoring the pH level of the fermentation medium the status of cell growth can be determined. The QD-polymer nanocomposites can be used as a pH sensor to detect the changes in pH of the fermentation medium. A continuous decrease in pH indicates an active cell growth process.

Furthermore, the QD-polymer nanocomposites can be used in drug delivery studies for chemical and biological sensing. pH-sensitive drug delivery systems, which are typically made of pH-sensitive hydrogel polymers with the drug encapsulated, are designed to deliver drugs under certain pH conditions, e.g. the pH present in the intestinal tract. During the development of such systems, the relationship between the efficiency of drug delivery and the pH condition needs to be studied. The QD-polymer nanocomposites can be applied in such studies to monitor drug release events under different pH conditions. For example, the QD-polymer nanocomposite pH sensor can be used for in-situ pH measurement in a solution where a pH-sensitive drug delivery system is tested. The drug that is released to the solution will change the pH, and the release rate can be determined by measuring the rate of pH change.

Additionally, the QD-polymer nanocomposite materials can be fabricated as nanoparticles that can be attached to a pH-sensitive drug delivery system. Certain mammal cells intake such drug delivery systems via processes such as endocytosis. Since the local pH within the cell changes in response to absorption of a drug, delivery of the drug inside a mammal cell can be detected by continuously monitoring the QD fluorescence.

Another chemical and biological detection application is water quality monitoring. Bacteria growth in water causes a change in pH of the water. Some changes in chemical composition will also cause a change in pH of the water. For example, water in a fish tank can become more acidic when contaminated by bacteria or as a result of a lack of oxygen. Since the response of the nanocomposites to pH is reversible, the QD-polymer nanocomposite can be used as a pH indicator in a fish tank, for example, to inform whether or not a water treatment is required.

Most industrial water treatment systems are dynamic because of seasonal variations in water chemistry and varying plant operating conditions. These and other factors affect the pH of the water, which can be monitored using QD-polymer nanocomposites.

In one working embodiment, a QD-polymer nanocomposite was produced using QDs that were purchased from Sigma-Aldrich Co, LLC of St. Louis, Mo., and without further purification were stably incorporated into a PAA-PHEMA-PEGDMA hydrogel polymer network. The formation of a PAA-PHEMA-PEGDMA hydrogel block copolymer has been previously described. (X. Li, *A Quartz Crystal Sensor for Monitoring the Polymerization, Expansion and Contraction of a Contractible Body*, 8th Pacific Centre for Advanced Materials and Microstructures, Burnaby, BC, Canada, Dec. 6, 2003). Such is a block co-polymer of acrylic acid (PAA), 2-hydroxyethyl methacrylate (PHEMA), ethylene glycol dimethacrylate (PEGDMA). A PAA-PEGDMA hydrogel polymer is prepared by first preparing a reaction precursor with a portion (e.g. 1.00 gram) of acrylic acid, 1 wt % (e.g. 0.01 gram) ethylene glycol dimethacrylate, and 6 wt % (e.g. 0.06 gram) 2,2-dimethoxy-2-phenylacetophenone. The mixture is then cured to form a hydrogel polymer using a UV lamp.

Example 1

Quantum dots having a core/shell structure of CdSe/ZnS suspended in toluene were purchased from Sigma-Aldrich Co. (#694622). The QDs were stabilized with a hexadecylamine (HAD) ligand coating surface treatment to have a fluorescence emission wavelength of 590 nm.

The QD suspension was dried prior to use, at room temperature and at 1 atm pressure overnight. Drying may alternatively be conducted under a vacuum to decrease drying time. For instance, under ambient conditions, drying takes approximately 6 hours while under a vacuum of 100 mm Hg pressure, such may be accomplished in approximately one half hour. The suspension should be dried until the liquid no longer flows, at which point the residue will have a wax-like appearance, and the time required to effectuate such is dependent upon the amount and concentration of the quantum dot suspension and the drying temperature and pressure.

A precursor solution was made with a 1:4 mole ratio of acrylic acid (AA) (Sigma-Aldrich Product #147230) to 2-hydroxyethyl methacrylate (HEMA) (Sigma-Aldrich Product #477028), 1 wt % ethylene glycol dimethacrylate (EGDMA) (Sigma-Aldrich Product #335681), 0.5 wt % of dried QDs and 6 wt % 2,2-dimethoxy-2-phenylacetophenone (photoinitiator) (Sigma-Aldrich Product #32782). While acrylic acid (AA) was used in this particular embodiment, those skilled in the art will recognize that other acrylic family monomers such as methacrylic acid (MAA) may be substituted for AA. Similarly, HEMA as used in this particular embodiment may be substituted for other acrylate monomers, for example, alkyl acrylates or alkyl methacrylates such as methacrylates, methyl acrylate, ethyl acrylate, butyl acrylate, butyl methacrylate, 2-ethylhexyl acrylate and isooctyl acrylate (IOA). Alternatively, hydroxyalkyl acrylates or hydroxyalkyl methacrylates including 2-hydroxyethyl acrylate (HEA) and hydroxymethyl methacrylate may be used in place of HEMA. A 2 μL volume of the precursor solution was placed on a glass surface using a micropipette and cured using a UV lamp and an exposure time of 14 seconds to form a film. The length of curing time is a function of the output energy of the UV lamp, the amount of precursor solution and the thickness of the precursor solution. Ethylene glycol dimethacrylate (EGDMA) was used as the cross-linking agent in this particular embodiment; however it will be apparent to those skilled in the art that other cross-linking agents may be employed without departing from the scope of the inventive concept of the subject Patent Application. Other cross-linking agents that can be used for AA and/or HEMA hydrogel polymerization include, for example, Tetraethylene glycol dimethacrylate (TEGDMA); Triethylene glycol dimethacrylate (TriEGDMA); Diethylene glycol dimethacrylate (DEGGMA); 1,1,1-trimethylol propane trimethacrylate; Methylene bisacrylamide (MBA) and N,N'-cystamine bis(acrylamide) (CBA).

Figure 1:
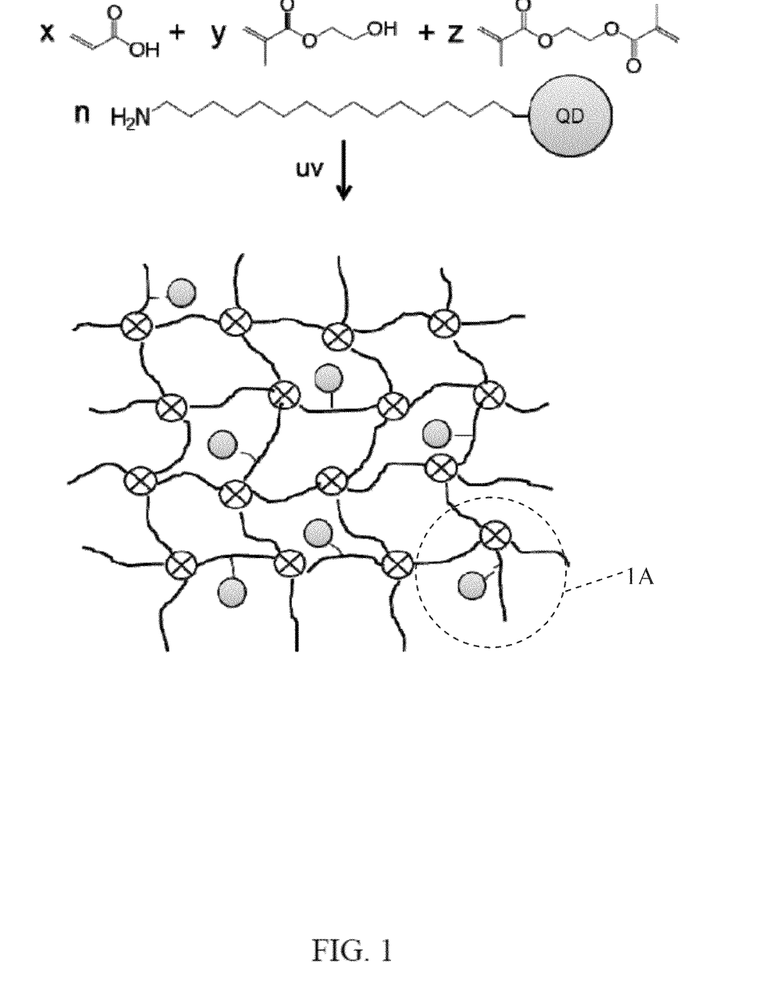
FIG. 1 is a schematic illustration of the formation of a nanocomposite of CdSe/ZnS QDs and PAA-PHEMA-PEGDMA hydrogel copolymer.
Figure 1A:
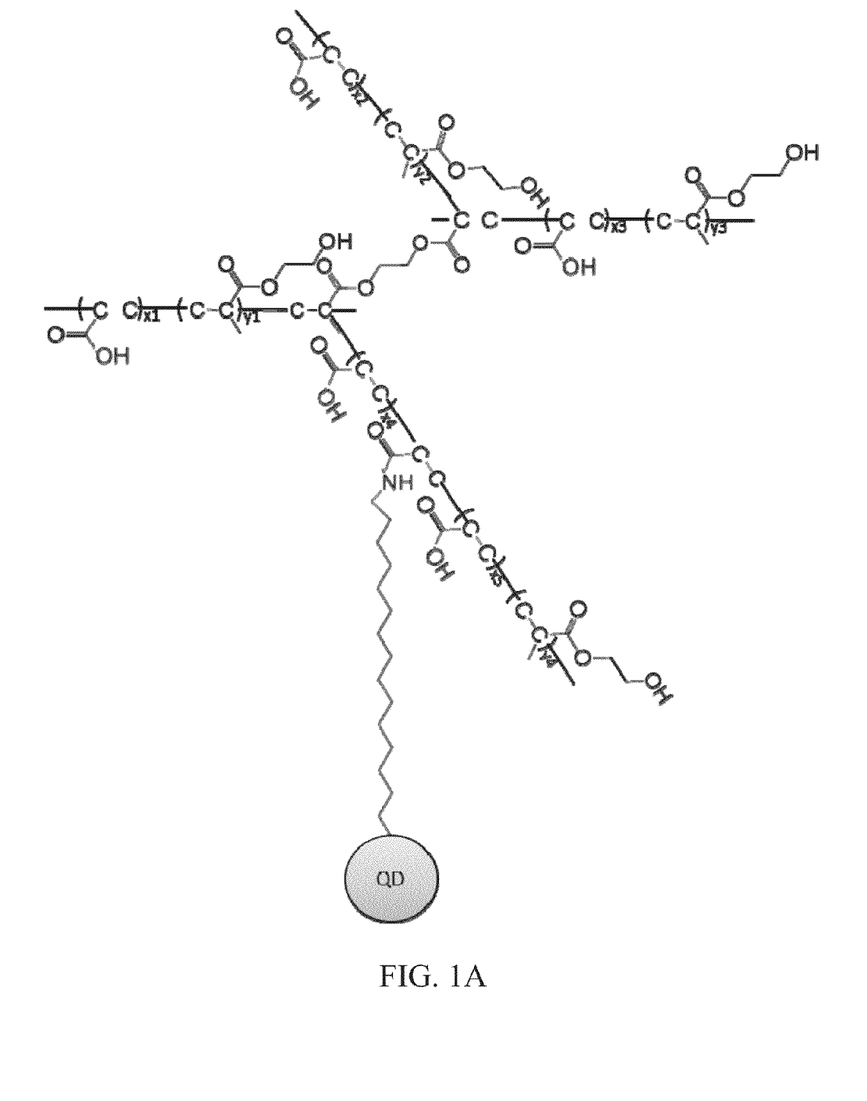
FIG. 1A is a two-dimensional representation of a portion of the nanocomposite showing the linkage between PEGDMA and four chains of PAA-PHEMA (hydrogel polymer) and the conjugation of the QD to the AA block of one of the PAA-PHEMA polymer chains.

FIG. 1 schematically illustrates the formation of a nanocomposite of CdSe/ZnS QDs and PAA-PHEMA-PEGDMA hydrogel copolymer. As the figure indicates, the QD is surface-functionalized with an amine groups and the acrylic acid (AA) has a carboxyl functional group. The functional amine groups on the QDs react with the carboxyl groups of acrylic acid (AA) to allow conjugation between the QDs and the AA block of the hydrogel copolymer as shown in FIG. 1A. While, in this case, conjugation occurred via the chemical interaction between the amine and carboxyl groups to form an amide, such provides only one example of possible reactivity between functional groups. That is to say that there are additional pairings of functional groups on the QD and polymer network that will enable a conjugation reaction to occur. For instance, the QD may be functionalized with hydroxyl groups for reacting with a carboxyl group on the polymer network. Conversely, it may be the QD which is functionalized with carboxyl groups to react with amine or hydroxyl groups on the polymer network. For example, amino alkyl acrylate monomers (e.g. amino ethyl methacrylate) or hydroxyl alkyl acrylate monomers (e.g. HEMA), in place of acrylic acid in the polymer network, can be conjugated with QDs functionalized with carboxyl groups.

Figure 2A:
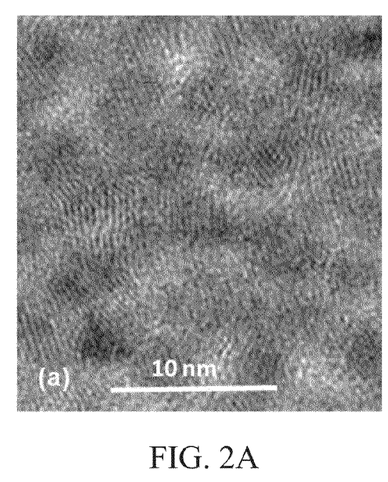
FIG. 2A is a TEM image of CdSe/ZnS QDs used to prepare the nanocomposite.
Figure 2B:
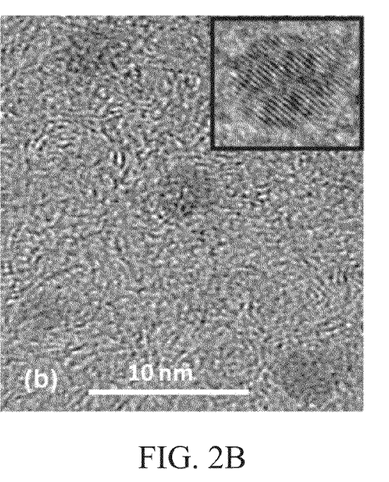
FIG. 2B is a TEM image of a CdSe/ZnS QD-polymer nanocomposite wherein darker regions represent incorporated QDs in the polymer network.

Samples of CdSe/ZnS QDs and the prepared nanocomposite were observed on a Transmission Electron Microscope (TEM) using an accelerating voltage of 10 kV, as shown in FIGS. 2A and 2B. Incorporation of the QDs into the polymer network was confirmed by the presence of visible darker regions with a pattern structure as can be clearly seen in FIG. 2B.

A nanocomposite hydrogel polymer network suitable for use in detecting the presence of a biological agent or chemical composition in solution, that effect the pH thereof, was prepared as a composite film. The nanocomposite hydrogel polymer was prepared on a glass cover slip in the manner previously described. Addition of 2 μL of water to the film created a neutral environment responsively and allowed for expansion of the copolymer network exposed thereto. Subsequently, the film was tested by the addition of 2 μL of 99.7% glacial acetic acid to a portion of the film. The reduced pH resultant acidic environment in the exposed portion of the film corresponded to contraction of the hydrogel network. Thereafter, 2 μL 30% NaOH solution was added to an adjacent portion of the hydrogel network to increase the pH in that region.

Figure 3:
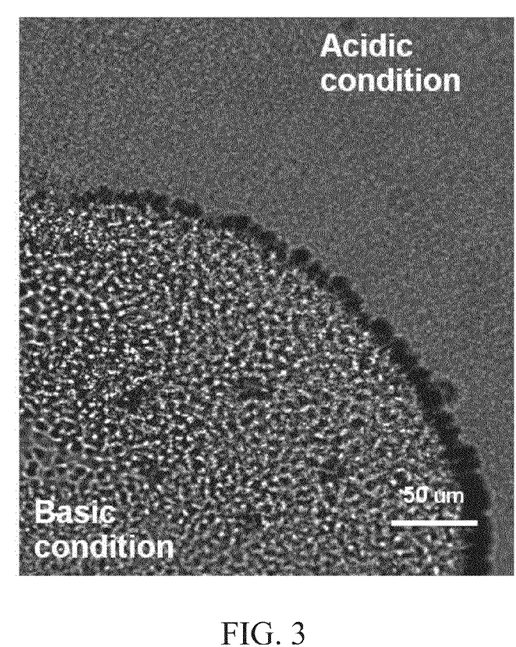
FIG. 3 is a fluorescence microscope image of the microstructure of the CdSe/ZnS QD-PAA-PHEMA-PEGDMA hydrogel copolymer nanocomposite exposed to acidic (top right) or basic (bottom left) condition to illustrate the difference in fluorescence resulting therefrom.

FIG. 3 is a fluorescence microscope image of the microstructure of the CdSe/ZnS QD-PAA-PHEMA-PEGDMA hydrogel copolymer nanocomposite under the respective acidic and basic conditions described above, and showing the difference in fluorescence therebetween. The expansion under basic conditions is attributable to dissociation of protons from the carboxyl group which causes negative-to-negative charge repulsion between polymer chains. The larger pores allow more excitation photons to reach the QDs and more emission photons to exit from the hydrogel copolymer nanocomposite to result in a measurably higher fluorescent intensity. Whereas, the shrinkage of the hydrogel copolymer nanocomposite network under acidic conditions increases internal light scattering of both excitation photons and emission photons. Therefore, under an acidic pH a measurable reduction in fluorescent intensity results for the CdSe/ZnS QD-PAA-PHEMA-PEGDMA hydrogel copolymer nanocomposite.

Figure 4:
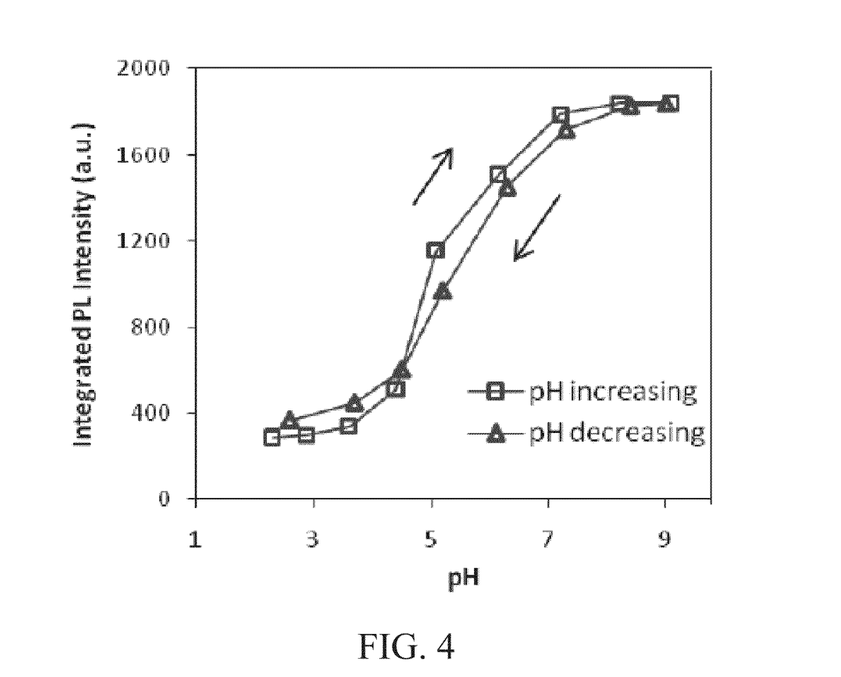
FIG. 4 is a graphical representation of the response of a CdSe/ZnS QD-PAA-PHEMA-PEGDMA hydrogel copolymer nanocomposite to bidirectional changes in pH conditions.

Similarly, a composite film was prepared on the sample holder of a NanoDrop fluorescence spectrometer and exposed to changes in pH. Initially, a 2 μL sample of 0.01M HCl was added to the film and fluorescence was measured. To increase pH, dilute 30% NaOH was gradually added to the solution. After each addition, the sample was excited by an excitation light source having a wavelength range overlapping that of the quantum dots in the nanocomposite and fluorescence was measured by an optical detection system. For example, a 390 nm light source was used for excitation when the quantum dots with an emission wavelength of 560 nm were used to prepare the nanocomposite, and the fluorescence at 560 nm was measured using a fluorescence spectrometer. In the instant example as shown in the graphs of FIG. 4, the high degree of fluorescence variation is indicative that fluorescence intensity dramatically increases when pH is between 4 and 7. The greater changes in fluorescence per unit of pH change when the pH is less than 7 indicates that, in this particular example, the hydrogel copolymer nanocomposite is more sensitive to changes in pH under acidic conditions. Since the pKa for acrylic acid falls within this pH range, the dissociation of $H^+$ ions from the —COOH group results in a large amount of negatively charged —COO$^-$ groups. These negatively charged groups repel one another causing expansion of the polymer network.

When the pH conditions are reversed to therefore decrease the pH, the change in fluorescence intensity is correspondingly reversed. Such reversible behavior verifies the stable incorporation of QDs into the polymer network structure. Thus, the stable incorporation of the QDs is such that the expansion of the polymer network does not release the QDs and nor does the contraction of the polymer network cause expulsion of the quantum dots therefrom.

Example 2

Figure 5:
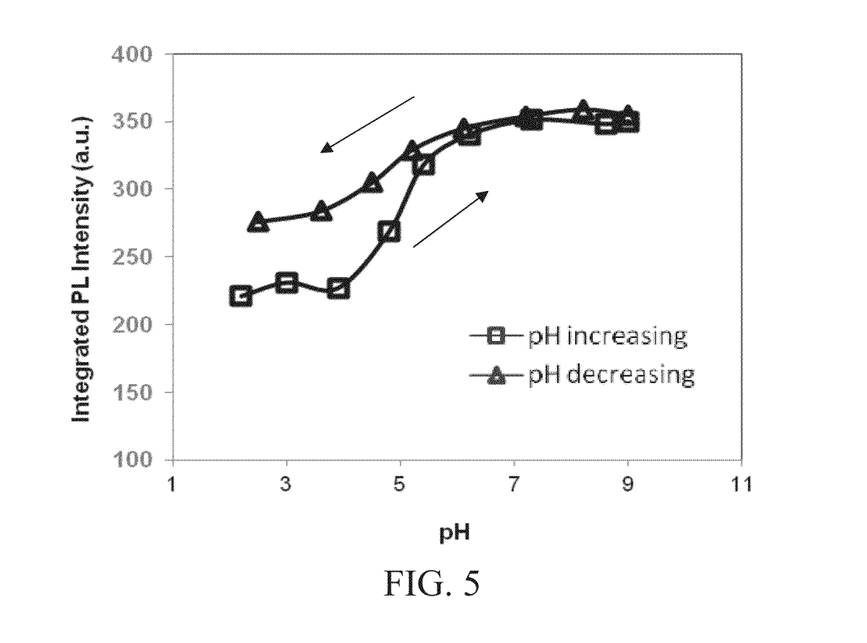
FIG. 5 is a graphical representation of the response of a CdSe/ZnS QD-PAA-PEGDMA hydrogel copolymer nanocomposite to bidirectional changes in pH conditions.

Another Experiment was conducted as set forth in Example 1, except that the hydrogel polymer network was only formed of a single type of monomer. Specifically, the precursor solution was made with a selected amount (e.g. 1.00 gram) of acrylic acid (AA) (Sigma-Aldrich Product #147230) to 1 wt % ethylene glycol dimethacrylate (EGDMA) (Sigma-Aldrich Product #335681), 0.5 wt % of dried QDs and 6 wt % 2,2-dimethoxy-2-phenylacetophenone (photoinitiator) (Sigma-Aldrich Product #32782). Such resulted in a CdSe/ZnS QD-PAA-PEGDMA nanocomposite. The response of this composite to pH changes in solution were measured in the manner as set forth with respect to Example 1. As the graphs in FIG. 5 indicate, the response of the CdSe/ZnS QD-PAA-PEGDMA nanocomposite is also shown to be reversible.

In certain other embodiments, after the quantum dot suspension is dried, the quantum dots are be dissolved in a solvent to form a solution. The solvent is one of acetone and dimethyl sulfoxide (DMSO). The dissolved quantum dot solution is then mixed with the monomers, a cross linking-agent and a photoinitiator to form the precursor solution for polymerization. The method proceeds as discussed above with regard to placement and curing of the precursor solution to form the nanocomposite.

Figure 6:
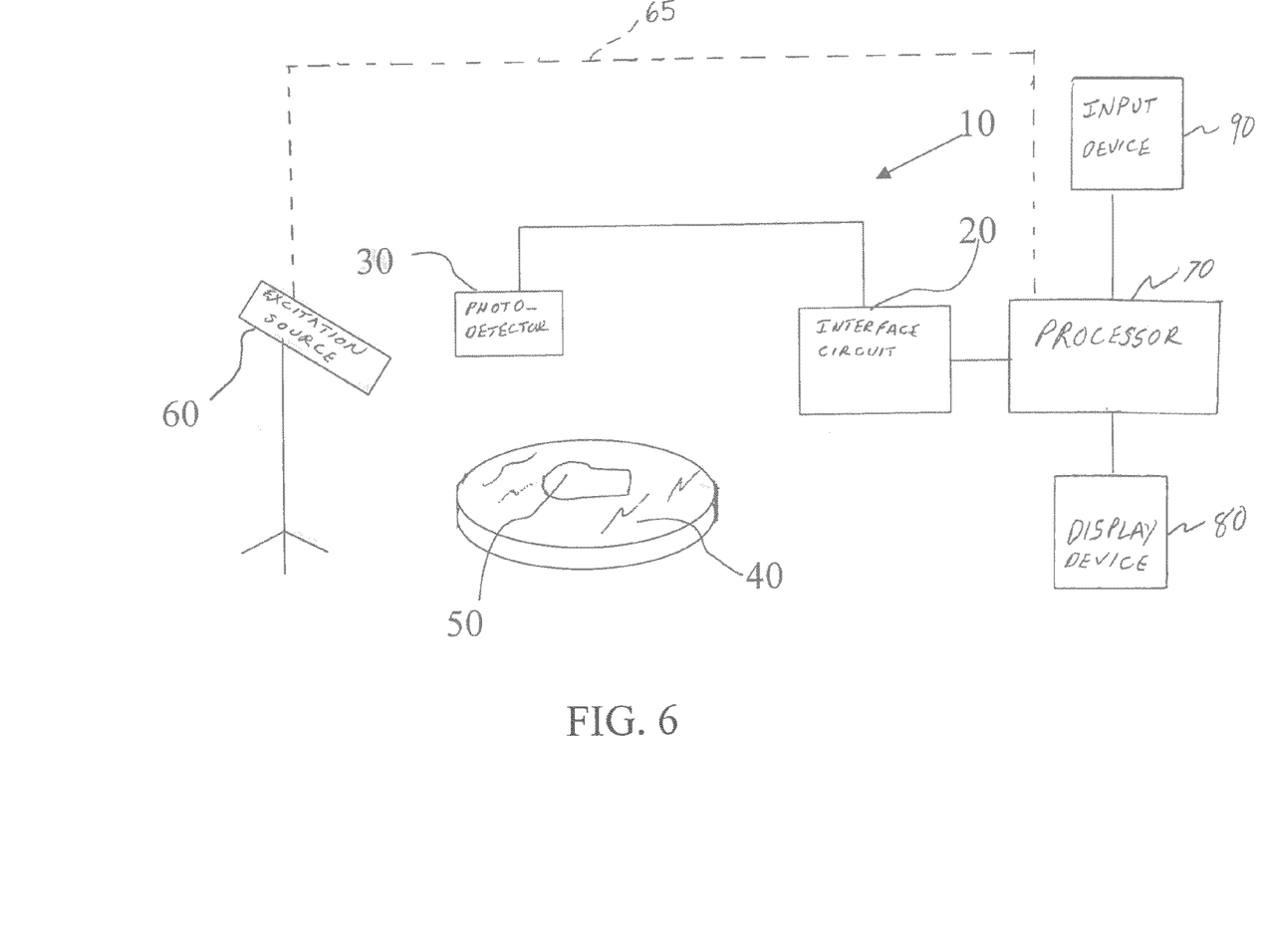
FIG. 6 shows an optical detection system for detecting the presence of a biological or chemical event in accordance with an embodiment of the present invention.

Referring now to FIG. 6, there is shown system 10 for optically detecting changes of the pH of a liquid 40 which is an aqueous solution as a means to detect the occurrence of a biological or chemical contamination of the liquid 40, where the biological agent or chemical composition of interest have an effect on the liquid's pH. The hydrogel copolymer nanocomposite 50, having quantum dots stably incorporated therein and which may be in the form of a film, is immersed in the liquid 40. For situations of ongoing monitoring, the film may be continually or periodically exposed to excitation illumination from the excitation source 60. The wavelength of excitation source 60 is chosen to be a wavelength that overlaps with the excitation wavelength of the quantum dots.

A photodetector 30 is located in a position to receive the fluorescent emission from the quantum dots in the hydrogel copolymer nanocomposite 50. Photodetector 50 may incorporate optical filters to exclude light in the wavelength range of the excitation source 60. The output of photodetector 30 is coupled to the interface circuit 20. The interface circuit 20 may incorporate digital and/or analog circuitry to establish a light intensity level from the electrical signal output from the photodetector 30 or simply convert an analog voltage output from photodetector 30 to a digital representation thereof for input to the processor 70. The output of interface circuit 20 is input to processor 70, which may include software for computing the light intensity corresponding to the voltage output by the photodetector 30 and software for establishing a pH value corresponding to the light intensity level of the quantum dot emissions. Processor 70 may also include software and sufficient storage to compute time related changes, such as averages and trends, and compute alerts when changes in the computed pH exceed stored threshold values. Processor 70 may provide a control signal through the link 65 to the excitation source 60 and corresponding software for controlling the periodic operation thereof. Thus, system 10 can monitor the liquid 40 over an extended time period and detect the contamination of the liquid 40 by a target chemical or biological agent as a result of the change in the pH value of the liquid 40 caused by the contamination.

Processor 70 has an output coupled to a display device 80. The computational results from processor 70 may be displayed on the display device 80, as will alerts and various parameters of system 10 monitored by processor 70. An input device 90 may also be coupled to processor 70 to permit entry of various parameters, such as pH alert threshold values and excitation source operating intervals. Processor 70, display device 80 and input device 90 may be incorporated in into a single device, such as a laptop computer, a tablet computer, a personal digital assistant (PDA), other mobile computing device, or the like. Such devices a particularly well suited for use by personnel performing discrete testing of liquids, such as a random inspection or an immediate investigation of possible contamination of liquids, such as bodies or containers of water, food or beverages, bodily fluids, etc.

The descriptions above are intended to illustrate possible implementations of the present invention and are not restrictive. While this disclosure has been made in connection with specific forms and embodiments thereof, it will be appreciated that various modifications other than those discussed above may be resorted to without departing from the spirit or scope of the claimed invention. Such variations, modifications, and alternatives will become apparent to the skilled artisan upon review of the disclosure. For example, functionally equivalent elements or method steps may be substituted for those specifically shown and described, and certain features may be used independently of other features, and in certain cases, particular locations of elements or sequence of method steps may be reversed or interposed, all without departing from the spirit or scope of the invention as defined in the appended Claims. The scope of the claimed invention should therefore be determined with reference to the description above and the appended claims, along with their full range of equivalents.

What is claimed is:

1. A quantum dot-polymer nanocomposite for optical sensing comprising: a plurality of quantum dots bound to a hydrogel polymer network formed from a mixture of a first monomer selected from the group consisting of acrylic acid (AA) and methacrylic acid (MAA) and an acrylate monomer using a cross-linking agent to form a pH responsive co-polymer, the quantum dot-polymer nanocomposite being in contact with a solution having an initial pH, wherein the addition of a biological or chemical contaminant generates a change in pH of the solution and thereby causes an expansion or contraction of the hydrogel polymer network, a light scattering effect of the polymer network and spacing between the plurality of quantum dots each change in correspondence to the expansion or contraction of the hydrogel polymer network and results in a change in a fluorescence emission intensity therefrom, wherein the change in pH is detected by measuring the change in quantum dot fluorescence emission intensity.

2. The quantum dot-polymer nanocomposite for optical sensing as claimed in claim 1, wherein the acrylate monomer is selected from the group consisting of 2-hydroxyethyl methacrylate (HEMA), 2-hydroxyethyl acrylate (HEA) and isooctyl acrylate (IOA).

3. The quantum dot-polymer nanocomposite for optical sensing as claimed in claim 1, wherein the cross-linking agent is ethylene glycol dimethacrylate.

4. The quantum dot-polymer nanocomposite for optical sensing as claimed in claim 1, wherein the quantum dots are functionalized with functional groups that react with functional groups of the hydrogel polymer network to allow conjugation between the quantum dots and the hydrogel polymer, wherein the functional groups on quantum dots are selected from the group consisting of amine, carboxyl and hydroxyl.

5. The quantum dot-polymer nanocomposite for optical sensing as claimed in claim 1, wherein a surface of the quantum dots is functionalized with groups selected to chemically react with the functional groups of the polymer network.

6. The quantum dot-polymer nanocomposite for optical sensing as claimed in claim 1, wherein the quantum dots are covalently bound to the polymer network.

7. The quantum dot-polymer nanocomposite for optical sensing as claimed in claim 1, wherein the quantum dots are stably conjugated with the copolymer network via chemical bonding, wherein the stable conjugation prevents the quantum dots from being expelled out of the polymer network during contraction whereby change in quantum dot fluorescence emission intensity is reversible.

8. A quantum dot-polymer nanocomposite for optical sensing comprising: a plurality of quantum dots distributed within a hydrogel polymer network formed from a mixture of a first monomer selected from the group consisting of acrylic acid (AA) and methacrylic acid (MAA) and an acrylate monomer using a cross-linking agent to form a pH responsive co-polymer, the quantum dots being functionalized to chemically bond to the hydrogel polymer network, the quantum dot-polymer nanocomposite being in contact with a solution having an initial pH, wherein the addition of a biological or chemical contaminant generates a change in pH of the solution and thereby causes an expansion or contraction of the hydrogel polymer network, a light scattering effect of the polymer network and spacing between the plurality of quantum dots change in correspondence to the expansion or contraction of the hydrogel polymer network and results in a change in a fluorescence emission intensity therefrom, wherein the change in pH is detected by measuring the change in quantum dot fluorescence emission intensity.

9. The quantum dot-polymer nanocomposite for optical sensing as claimed in claim 8, wherein the chemical bond is a conjugation between functional groups on the surface of the quantum dots and the hydrogel polymer.

10. The quantum dot-polymer nanocomposite for optical sensing as claimed in claim 8, wherein the chemical bond is a covalent bond to the hydrogel polymer.

11. The quantum dot-polymer nanocomposite for optical sensing as claimed in claim 8, wherein functional groups on the surface of the quantum dots are selected from the group consisting of amine, carboxyl and hydroxyl.

12. The quantum dot-polymer nanocomposite for optical sensing as claimed in claim 9, wherein the functional groups on the surface of the quantum dots are selected from the group consisting of amine, carboxyl and hydroxyl.

13. The quantum dot-polymer nanocomposite for optical sensing as claimed in claim 8, wherein the quantum dots are functionalized on a surface thereof with groups selected to chemically bond with functional groups of the hydrogel polymer.

14. The quantum dot-polymer nanocomposite for optical sensing as claimed in claim 8, wherein the acrylate monomer is selected from the group consisting of 2-hydroxyethyl methacrylate (HEMA), 2-hydroxyethyl acrylate (HEA) and isooctyl acrylate (IOA).

15. The quantum dot-polymer nanocomposite for optical sensing as claimed in claim 8, wherein the cross-linking agent is ethylene glycol dimethacrylate.

16. The quantum dot-polymer nanocomposite for optical sensing as claimed in claim 14, wherein the cross-linking agent is ethylene glycol dimethacrylate.

17. A quantum dot-polymer nanocomposite for optical sensing comprising: a plurality of quantum dots bound to a hydrogel polymer network formed from at least a mixture of a first monomer selected from the group consisting of acrylic acid (AA) and methacrylic acid (MAA) and an acrylate monomer to form a pH responsive co-polymer, the quantum dot-polymer nanocomposite being in contact with a solution having an initial pH, wherein the addition of a biological agent or chemical contaminant generates a change in pH of the solution and a corresponding reversible change in physical size of the hydrogel polymer network, a light scattering effect of the polymer network and spacing between the plurality of quantum dots change in correspondence to the change in physical size of the hydrogel polymer network and results in a change in a fluorescence emission intensity therefrom in response to impingement by an excitation light source, wherein the change in pH is detected by measuring the change in quantum dot fluorescence emission intensity.

* * * * *